(12) United States Patent
Ishikawa et al.

(10) Patent No.: US 12,112,474 B2
(45) Date of Patent: Oct. 8, 2024

(54) IMAGE EXTRACTION DEVICE, IMAGE EXTRACTION SYSTEM, IMAGE EXTRACTION METHOD, AND IMAGE EXTRACTION PROGRAM

(71) Applicant: The University of Tokyo, Tokyo (JP)

(72) Inventors: Shumpei Ishikawa, Tokyo (JP); Daisuke Komura, Tokyo (JP); Akihiro Kawabe, Tokyo (JP)

(73) Assignee: The University of Tokyo, Tokyo (JP)

( * ) Notice: Subject to any disclaimer, the term of this patent is extended or adjusted under 35 U.S.C. 154(b) by 368 days.

(21) Appl. No.: 17/620,328

(22) PCT Filed: Jun. 17, 2020

(86) PCT No.: PCT/JP2020/023749
§ 371 (c)(1),
(2) Date: Dec. 17, 2021

(87) PCT Pub. No.: WO2020/256011
PCT Pub. Date: Dec. 24, 2020

(65) Prior Publication Data
US 2022/0245804 A1    Aug. 4, 2022

(30) Foreign Application Priority Data

Jun. 19, 2019  (JP) ................. 2019-113730

(51) Int. Cl.
*G06T 7/00* (2017.01)
*G06V 10/82* (2022.01)
*G16H 30/20* (2018.01)

(52) U.S. Cl.
CPC ............ *G06T 7/0012* (2013.01); *G06V 10/82* (2022.01); *G16H 30/20* (2018.01); *G06T 2207/10056* (2013.01)

(58) Field of Classification Search
CPC ........ G06T 7/0012; G06T 2207/10056; G16H 30/20; G06V 10/82
See application file for complete search history.

(56) References Cited

U.S. PATENT DOCUMENTS

2008/0152225 A1*  6/2008  Iwamoto .............. G06V 10/758
382/190

FOREIGN PATENT DOCUMENTS

| CN | 109872362 A | * | 6/2019 |
| JP | 2009-9290 A | * | 1/2009 |

(Continued)

OTHER PUBLICATIONS

L.A. Gatys et al., "Image Style Transfer Using Convolutional Neural Networks," IEEE Conference on Computer Vision and Pattern Recognition (CVPR), pp. 2414-2423 (2016).

(Continued)

*Primary Examiner* — Khai M Nguyen
(74) *Attorney, Agent, or Firm* — Mintz Levin Cohn Ferris Glovsky and Popeo, P.C.

(57) ABSTRACT

An image extraction device, an image extraction system, an image extraction method, and an image extraction program are capable of extracting an appropriate reference image from a database by using a pathological image as a query. The image extraction device includes: an acquisition unit which acquires a pathological image; a first calculation unit which calculates a local feature amount of the pathological image; a second calculation unit which calculates a non-local feature amount based on a correlation with the local feature amount; a third calculation unit which calculates a degree of similarity between the non-local feature amount and a feature amount of each of a plurality of reference (Continued)

images stored in a database; and an extraction unit which extracts one or more reference images based on the degree of similarity.

14 Claims, 10 Drawing Sheets

(56) References Cited

FOREIGN PATENT DOCUMENTS

| | | |
|---|---|---|
| JP | 2018-050671 A | 4/2018 |
| JP | 2018-180635 A | 11/2018 |

OTHER PUBLICATIONS

International Search Report issued Sep. 15, 2020 in corresponding PCT Application No. PCT/JP2020/023749.

\* cited by examiner

IMAGE EXTRACTION DEVICE, IMAGE EXTRACTION SYSTEM, IMAGE EXTRACTION METHOD, AND IMAGE EXTRACTION PROGRAM

CROSS-REFERENCE OF RELATED APPLICATION

This application is a U.S. National Phase of International Application No. PCT/JP2020/023749 with an International Filing Date of Jun. 17, 2020, which claims under 35 U.S.C. § 119(a) the benefit of Japanese patent application No. 2019-113730 filed on Jun. 19, 2019, the entire contents of which are incorporated herein by reference.

TECHNICAL FIELD

The present invention relates to an image extraction device, an image extraction system, an image extraction method, and an image extraction program.

BACKGROUND ART

Conventionally, a pathological diagnosis based on an image of pathological tissue of a person to be diagnosed has been made. A doctor who makes the pathological diagnosis based on the pathological image may refer to an atlas to search for similar images in order to identify a medical case.

On the other hand, image analysis technology using neural networks has been developed in recent years and, for example, in Non-Patent Document 1 below, technology for transferring an image style into a painting style is described.

CITATION LIST

Non-Patent Document

Non-Patent Document 1: Leon A. Gatys, Alexander S. Ecker, and Matthias Bethge, "Image Style Transfer Using Convolutional Neural Networks," IEEE Conference on Computer Vision and Pattern Recognition (CVPR), 2016.

SUMMARY

Technical Problem

Conventionally, an atlas of digitized pathological images has been used, but an image search may be made by using text as a query. However, when a pathological image is searched for, it is difficult to set an appropriate query in a case of a medical case that is difficult to interpret or a first-time medical case, and it may be difficult to extract reference images.

Therefore, the present invention provides an image extraction device, an image extraction system, an image extraction method, and an image extraction program capable of extracting an appropriate reference image from a database by using a pathological image as a query.

Solution to Problem

An image extraction device according to one aspect of the present invention includes: an acquisition unit which acquires a pathological image; a first calculation unit which calculates a local feature amount of the pathological image; a second calculation unit which calculates a non-local feature amount based on a correlation with the local feature amount; a third calculation unit which calculates a degree of similarity between the non-local feature amount and a feature amount of each of a plurality of reference images stored in a database; and an extraction unit which extracts one or more reference images based on the degree of similarity.

According to this aspect, an appropriate reference image can be extracted from the database by using the pathological image as a query as a result of calculating the non-local feature amount of the pathological image and comparing the non-local feature amount with the feature amount of each of the plurality of reference images stored in the database.

In the above aspect, the image extraction device may further include a display unit which displays at least either one of the extracted one or more reference images, identification information of the one or more reference images, the type of pathology related to the one or more reference images, and the degree of similarity between the one or more reference images and the pathological image.

According to this aspect, information related to the extracted one or more reference images can be checked, and this can make it easier to evaluate a relation with the pathological image as the query.

In the above aspect, the first calculation unit may also calculate the local feature amount using a feature map calculated by a hidden layer included in a pre-trained convolutional neural network.

According to this aspect, a feature amount properly representing a local feature of the pathological image can be calculated.

In the above aspect, the second calculation unit may also calculate the non-local feature amount based on a correlation with a feature map calculated by a hidden layer included in a pre-trained convolutional neural network.

According to this aspect, a feature amount properly representing a non-local feature of the pathological image can be calculated.

In the above aspect, the second calculation unit may further calculate the non-local feature amount based on a correlation between two kinds of feature maps calculated by different hidden layers included in a pre-trained convolutional neural network.

According to this aspect, a feature amount properly representing a non-local feature of the pathological image can be calculated.

In the above aspect, the second calculation unit may further calculate the non-local feature amount based on a correlation between two kinds of feature maps calculated by hidden layers included in two kinds of pre-trained convolutional neural networks.

According to this aspect, a feature amount properly representing a local feature of the pathological image can be calculated.

In the above aspect, the plurality of reference images may include images cut out at random from regions selected in a whole slide image of pathological tissue.

According to this aspect, a reference image properly representing the feature of pathological tissue can be extracted.

In the above aspect, the image extraction device may further include a determination unit which determines whether or not a certain gene mutation occurs in a cell captured in the pathological image based on the non-local feature amount.

According to this aspect, it can be predicted whether or not the certain gene mutation occurs by using the pathological image as a query.

In the above aspect, the image extraction device may further include a generation unit which uses, as training data, a first image of a certain pathology, in which a cell with a certain gene mutation occurring therein is captured, and a second image of the certain pathology, in which cells without occurrence of the certain gene mutation are captured, to generate a determination model used to determine whether or not the certain gene mutation occurs in a cell captured in the pathological image based on the non-local feature amount.

According to this aspect, a determination model used to determine whether or not a certain gene mutation occurs can be generated by using the pathological image as a query.

In the above aspect, the image extraction device may further include a display unit which, when it is determined by the determination model that the certain gene mutation occurs, displays a region of the pathological image as the basis of the determination.

According to this aspect, the basis of determining that the certain gene mutation occurs can be visually checked.

An image extraction system according to another aspect of the present invention is an image extraction system including an image extraction device and a user terminal, wherein the user terminal has an imaging unit for taking a pathological image, and the image extraction device has: an acquisition unit which acquires the pathological image; a first calculation unit which calculates a local feature amount of the pathological image; a second calculation unit which calculates a non-local feature amount based on a correlation with the local feature amount; a third calculation unit which calculates a degree of similarity between the non-local feature amount and a feature amount of each of a plurality of reference images stored in a database; and an extraction unit which extracts one or more reference images based on the degree of similarity.

According to this aspect, an appropriate reference image can be extracted from the database by using the pathological image as a query as a result of calculating the non-local feature amount of the pathological image and comparing the non-local feature amount with the feature amounts of the plurality of reference images stored in the database.

In the above aspect, the user terminal may further have a display unit which displays at least either one of the extracted one or more reference images, identification information of the one or more reference images, the type of pathology related to the one or more reference images, and the degree of similarity between the one or more reference images and the pathological image.

According to this aspect, information related to the extracted one or more reference images can be checked, and this can make it easier to evaluate a relation with the pathological image as the query.

An image extraction method according to still another aspect of the present invention includes: acquiring a pathological image; calculating a local feature amount of the pathological image; calculating a non-local feature amount based on a correlation with the local feature amount; calculating a degree of similarity between the non-local feature amount and a feature amount of each of a plurality of reference images stored in a database; and extracting one or more reference images based on the degree of similarity.

According to this aspect, an appropriate reference image can be extracted from the database by using the pathological image as a query as a result of calculating the non-local feature amount of the pathological image and comparing the non-local feature amount with the feature amounts of the plurality of reference images stored in the database.

An image extraction program according to yet another aspect of the present invention causes an arithmetic unit included in an image extraction device to function as: an acquisition unit which acquires a pathological image; a first calculation unit which calculates a local feature amount of the pathological image; a second calculation unit which calculates a non-local feature amount based on a correlation with the local feature amount; a third calculation unit which calculates a degree of similarity between the non-local feature amount and a feature amount of each of a plurality of reference images stored in a database; and an extraction unit which extracts one or more reference images based on the degree of similarity.

According to this aspect, an appropriate reference image can be extracted from the database by using the pathological image as a query as a result of calculating the non-local feature amount of the pathological image and comparing the non-local feature amount with the feature amounts of the plurality of reference images stored in the database.

Advantageous Effects of Invention

According to the present invention, there can be provided an image extraction device capable of extracting an appropriate reference image from a database by using a pathological image as a query, a pathological image extraction method, and a pathological image extraction program.

DESCRIPTION OF EMBODIMENT

An embodiment of the present invention will be described with reference to the accompanying drawings. Note that the same reference numeral given in respective drawings has the same or similar component.

Figure 1:
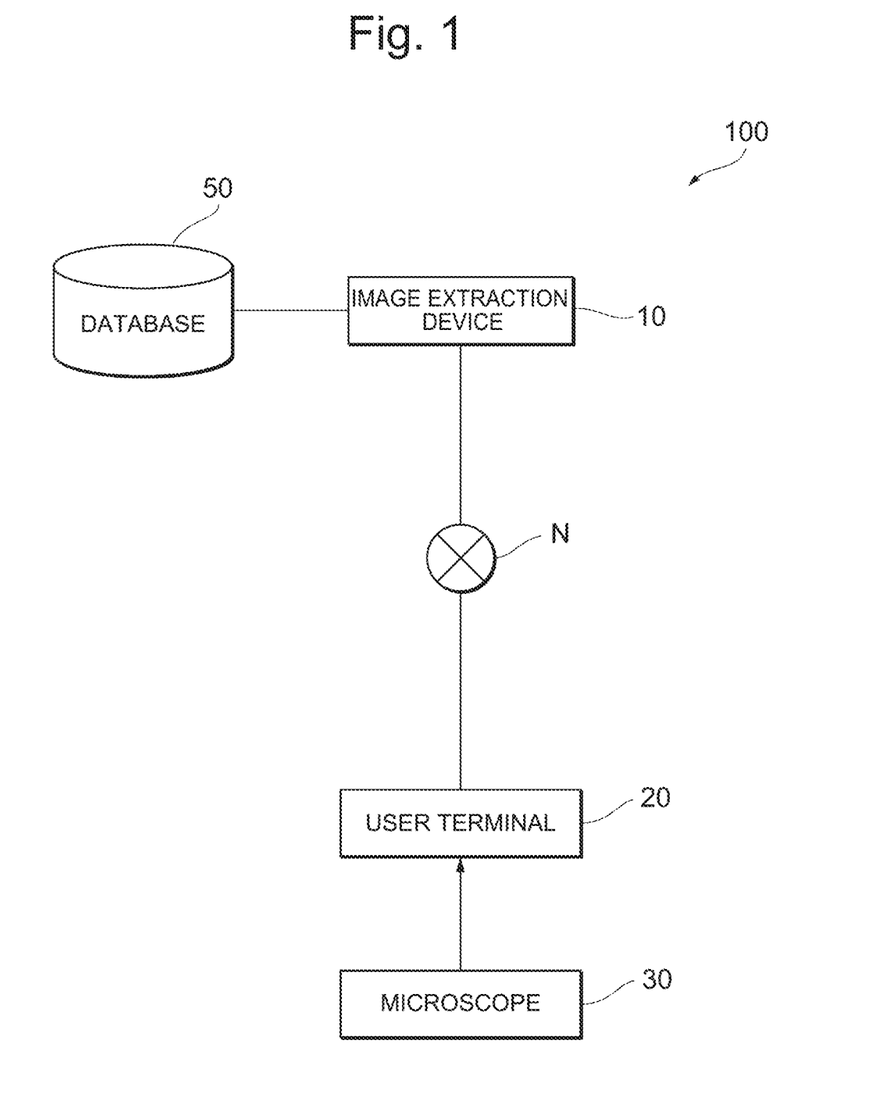
FIG. 1 is a diagram illustrating the network configuration of an image extraction system according to an embodiment of the present invention.

FIG. 1 is a diagram illustrating the network configuration of an image extraction system 100 according to the embodiment of the present invention. The image extraction system 100 includes an image extraction device 10 and a user terminal 20. The image extraction device 10 and the user terminal 20 may be general-purpose computers, or the user terminal 20 may also be a smartphone, for example.

A user observes the pathological tissue of a subject with a microscope 30 and takes a pathological image using the user terminal 20. The taken pathological image is sent from the user terminal 20 to the image extraction device 10 through a communication network N such as the Internet.

The image extraction device 10 uses the acquired pathological image as a query to extract one or more reference images stored in a database 50. The image extraction device 10 may display the extracted reference images on a display unit of the image extraction device 10 or transmit the extracted reference images to the user terminal 20.

Figure 2:
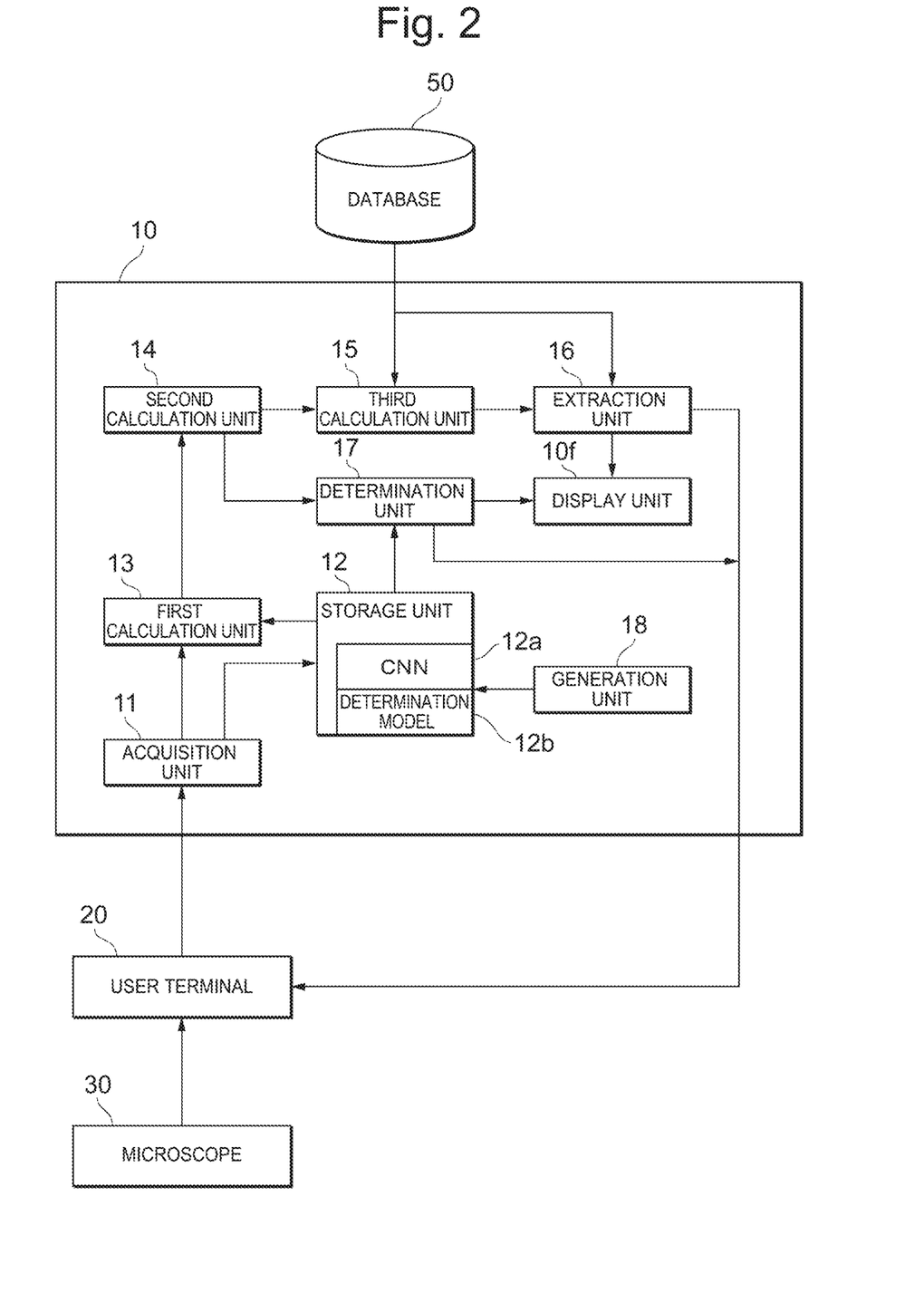
FIG. 2 is a diagram illustrating functional blocks of an image extraction device according to the present embodiment.

FIG. 2 is a diagram illustrating functional blocks of the image extraction device 10 according to the present embodiment. The image extraction device 10 includes an acquisition unit 11, a storage unit 12, a first calculation unit 13, a second calculation unit 14, a third calculation unit 15, an extraction unit 16, a determination unit 17, and a generation unit 18.

The acquisition unit 11 acquires the pathological image. The acquisition unit 11 may acquire the pathological image from the user terminal 20 or acquire the pathological image from any other device. Further, when an imaging unit is provided in the image extraction device 10, the acquisition unit 11 may acquire the pathological image from the imaging unit concerned.

The storage unit 12 stores a convolutional neural network (CNN) 12a and a determination model 12b. The convolutional neural network 12a may be a pre-trained model, and a model proposed, for example, in Simonyan, Karen and Zisserman, Andrew, "Very Deep Convolutional Networks for Large-Scale Image Recognition," arXiv 1409.1556, 2014, may be used. The image extraction device 10 calculates a local feature amount of the pathological image by the convolutional neural network 12a.

The determination model 12b is a model used to determine whether or not a certain gene mutation occurs in a cell(s) captured in the pathological image. The determination model 12b may be configured by using any algorithm, or by using a neural network, a support vector machine, or the like.

The first calculation unit 13 calculates the local feature amount of the pathological image. The first calculation unit 13 may calculate the local feature amount using a feature map calculated by a hidden layer included in the pre-trained convolutional neural network 12a. In this specification, a feature map of the i-th filter related to a position j of the L-th layer included in the convolutional neural network 12a is denoted by A feature amount properly representing a local feature of the pathological image can be calculated by the pre-trained convolutional neural network 12a.

The second calculation unit 14 calculates a non-local feature amount based on a correlation with the local feature amount. The second calculation unit 14 may calculate the non-local feature amount based on a correlation with the feature map calculated by the hidden layer included in the pre-trained convolutional neural network 12a. The second calculation unit 14 may calculate a non-local feature amount $G^L_{ij}$ by $G^L_{ij} = \Sigma_k F^L_{ik} F^L_{jk}$. By the second calculation unit 14, a feature amount properly representing the non-local feature of the pathological image can be calculated.

The second calculation unit 14 may use Compact Bilinear Pooling described in Yang Gao, Oscar Beijbom, Ning Zhang, and Trevor Darrell, "Compact Bilinear Pooling," arXiv:1511.06062, 2015, to transform the non-local feature amount to a feature amount of about 1024 dimensions. However, the second calculation unit 14 may also transform the non-local feature amount to the feature amount of about 1024 dimensions by any other method such as principal component analysis.

The second calculation unit 14 may also calculate the non-local feature amount based on a correlation between two kinds of feature maps calculated by different hidden layers included in the pre-trained convolutional neural network 12a. In other words, the second calculation unit 14 may use a feature map $F^L_{ik}$ in an L layer and a feature map $F^M_{jk}$ in an M layer included in the convolutional neural network 12a to calculate a non-local feature amount $G^{L,M}_{ij}$ by $G^{L,M}_{ij} = \Sigma_k F^L_{ik} F^M_{jk}$. Thus, a feature amount properly representing the non-local feature of the pathological image can be calculated.

Further, the second calculation unit 14 may calculate the non-local feature amount based on a correlation between two kinds of feature maps calculated by hidden layers included in two kinds of pre-trained convolutional neural networks. In other words, the second calculation unit 14 may use a feature map $F^L_{ik}$ in an L layer included in a first convolutional neural network and a feature map $F^M_{jk}$ in an M layer included in a second convolutional neural network to calculate the non-local feature amount $G^{L,M}_{ij}$ by $G^{L,M}_{ij} = \Sigma_k F^L_{ik} F^M_{jk}$. Thus, a feature amount properly representing the non-local feature of the pathological image can be calculated.

The third calculation unit 15 calculates a degree of similarity between the non-local feature amount and each of feature amounts of a plurality of reference images stored in the database 50. The plurality of reference images stored in the database 50 includes images cut out at random from regions selected in a whole slide image of pathological tissue. By storing such reference images in the database 50, a reference image properly representing the feature of the pathological tissue can be extracted. Further, the database 50 may also store the plurality of reference images and non-local feature amounts respectively calculated for the plurality of reference images in association with one another. The third calculation unit 15 may also calculate a degree of similarity between the non-local feature amount calculated for the pathological image and each of non-local feature amounts of reference images stored in the database 50.

The extraction unit 16 extracts one or more reference images based on the degree of similarity calculated by the third calculation unit 15. The extraction unit 16 may also extract, from the database 50, a reference image having a higher predetermined percentage of the degree of similarity.

According to the image extraction device 10 according to the present embodiment, an appropriate reference image can be extracted from the database 50 by using the pathological image as a query as a result of calculating the non-local feature amount of the pathological image and comparing the non-local feature amount with the feature amounts of the plurality of reference images stored in the database.

The image extraction device 10 may select which layer's feature map is used from among a plurality of hidden layers included in a plurality of pre-trained neural networks as follows: First, a pathologist extracts, from the database 50, a plurality of reference images similar to a query image in descending order of similarity. Then, the same query image is input to the plurality of pre-trained neural networks to calculate respective non-local feature amounts by using feature maps in the plurality of hidden layers. Next, degrees of similarity between the non-local feature amount and the feature amounts of the plurality of reference images stored in the database 50 are calculated respectively for each of calculation methods to extract a plurality of reference images in descending order of similarity. The image extraction device 10 may calculate rank correlations between the plurality of reference images extracted by a plurality of calculation methods and the plurality of reference images extracted by the pathologist to select the most correlated calculation method.

A display unit 10f displays at least either one of the extracted one or more reference images, identification information of the one or more reference images, the type of pathology related to the one or more reference images, and the degree of similarity between the one or more reference images and the pathological image. Here, for example, the identification information of the one or more reference images may be the ID(s) of the Cancer Genome Atlas (TCGA). Further, for example, the type of pathology related to the one or more reference images may be the type of cancer. Thus, information related to the extracted one or more reference images can be checked by displaying information related to the extracted reference images, and this makes it easier to evaluate a relation with the pathological image as the query.

The user terminal 20 may also have a display unit for displaying at least either one of the one or more reference images extracted by the image extraction device 10, the identification information of the one or more reference images, the type of pathology related to the one or more reference images, and the degree of similarity between the one or more reference images and the pathological image. Thus, the user can use the user terminal 20 such as the smartphone to check the information related to the extracted one or more reference images, and this makes it easier to evaluate a relation with the pathological image as the query.

Based on the non-local feature amount, the determination unit 17 determines whether or not a certain gene mutation occurs in a cell captured in the pathological image. Based on the non-local feature amount of the pathological image calculated by the second calculation unit 14, the determination unit 17 may also use the determination model 12b to determine whether or not the certain gene mutation occurs in the cell captured in the pathological image. Thus, by using the pathological image as the query, it can be predicted whether or not the certain gene mutation occurs.

The generation unit 18 uses, as training data, a first image of a certain pathology in a captured cell with the certain gene mutation occurring therein and a second image of the certain pathology in captured cells without occurrence of the certain gene mutation to generate the determination model 12b used to determine, based on the non-local feature amount, whether or not the certain gene mutation occurs in the cell captured in the pathological image. The determination model 12b may also be a model such as a neural network trained to determine whether or not the certain gene mutation occurs in the cell captured in the pathological image based on the non-local feature amount of the pathological image by using, as training data, the first image, in which the cell with a certain gene mutation occurring therein about a specific type of cancer is captured, and the second image in which cells without occurrence of the certain gene mutation are captured. Here, the first image in which the cell with the certain gene mutation occurring therein is captured, and the second image in which the cells without occurrence of the certain gene mutation are captured may be collected by the pathologist, respectively. The determination model 12b used to determine whether or not the certain gene mutation occurs by using the pathological image as the query can be generated by the generation unit 18.

When it is determined by the determination model 12b that the certain gene mutation occurs, the display unit 10f may also display a region of the pathological image as the basis of the determination. The image extraction device 10 may represent, as a heat map, the region of the pathological image to which the determination model 12b pays attention by using a method, for example, proposed in Ramprasaath R. Selvaraju, Michael Cogswell, Abhishek Das, Ramakrishna Vedantam, Devi Parikh, and Dhruv Batra, "Grad-CAM: Visual Explanations from Deep Networks via Gradient-based Localization," arXiv:1610.02391, 2016, and display the region on the display unit 10f. Thus, the basis of determining that the certain gene mutation occurs can be visually checked.

Figure 3:
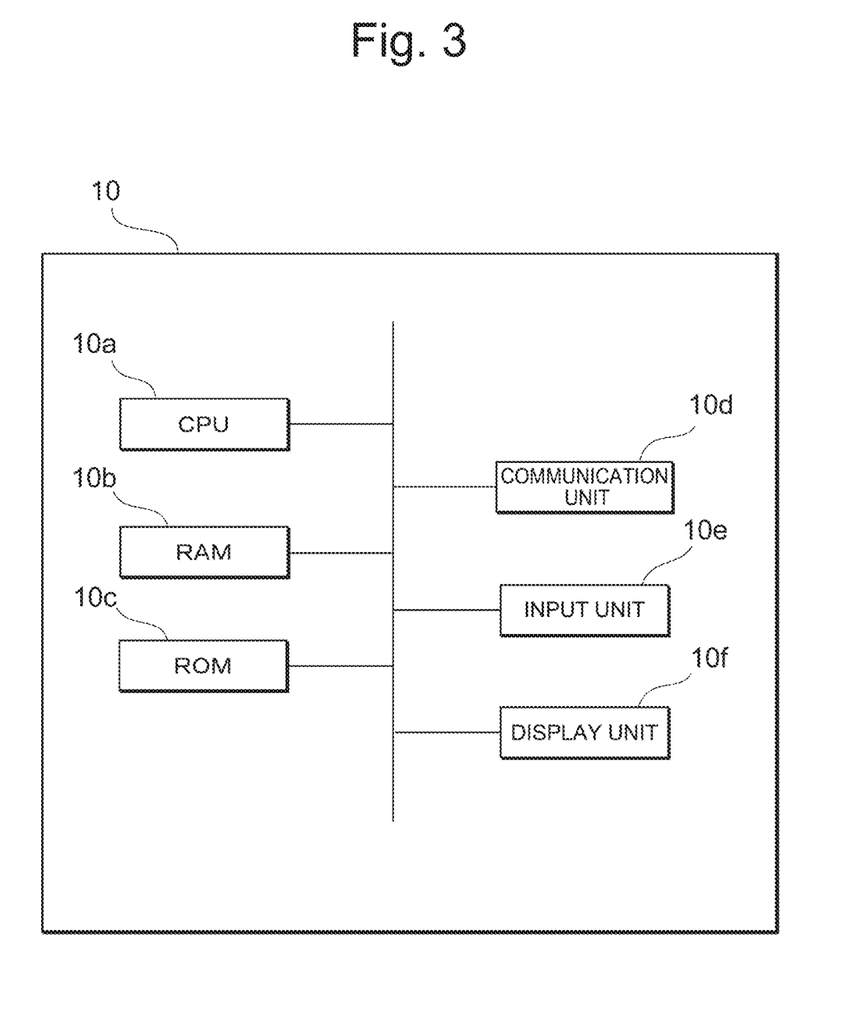
FIG. 3 is a diagram illustrating the physical configuration of the image extraction device according to the present embodiment.

FIG. 3 is a diagram illustrating the physical configuration of the image extraction device 10 according to the present embodiment. The image extraction device 10 has a CPU (Central Processing Unit) 10a corresponding to an arithmetic unit, a RAM (Random Access Memory) 10b and a ROM (Read only Memory) 10c corresponding to a storage unit, a communication unit 10d, an input unit 10e, and the display unit 10f. These components are connected to one another through a bus in a manner to be able to send and receive data. Note that a case where the image extraction device 10 is one computer is described in this example, but the image extraction device 10 may also be realized by combining two or more computers. Further, the configuration illustrated in FIG. 3 is just an example, and the image extraction device 10 may also have any component other than these components, or may not have some of these components.

The CPU 10a is a control unit for performing control related to the execution of programs stored in the RAM 10b or the ROM 10c and performing data calculation and processing. The CPU 10a is an arithmetic unit to execute a program (image extraction program) for extracting reference images stored in the database based on the pathological image. The CPU 10a receives various data from the input unit 10e and the communication unit 10d to display data calculation results on the display unit 10f and store the data calculation results in the RAM 10b.

The RAM 10b is data rewritable one in the storage unit, which may be composed of semiconductor memory elements, for example. The RAM 10b may store the programs executed by the CPU 10a and data such as the pathological image. Note that these are illustrative examples, and any data other than these data may be stored in the RAM 10b or some of these data may not be stored.

The ROM 10c is data readable one in the storage unit, which may be composed of semiconductor memory elements, for example. For example, the ROM 10c may store the image extraction program and data which is not rewritten.

The communication unit 10d is an interface to connect the image extraction device 10 to any other device. The communication unit 10d may be connected to the communication network N such as the Internet.

The input unit 10e accepts data input from the user, which may include a keyboard and a touch panel, for example.

The display unit 10f visually displays the calculation results of the CPU 10a, which may be an LCD (Liquid Crystal Display), for example. For example, the display unit 10f may display the pathological image and the extracted one or more reference images.

The image extraction program may be provided by being stored on a computer readable storage medium, such as the RAM 10b or the ROM 10c, or provided through a communication network connected by the communication unit 10d. In the image extraction device 10, the CPU 10a executes the image extraction program to realize various operations described with reference to FIG. 2. Note that these physical components are illustrative examples, and each component may not be necessarily an independent component. For example, the image extraction device 10 may include an LSI (Large-Scale Integration) in which the CPU 10a, the RAM 10b, and the ROM 10c are integrated.

Figure 4:
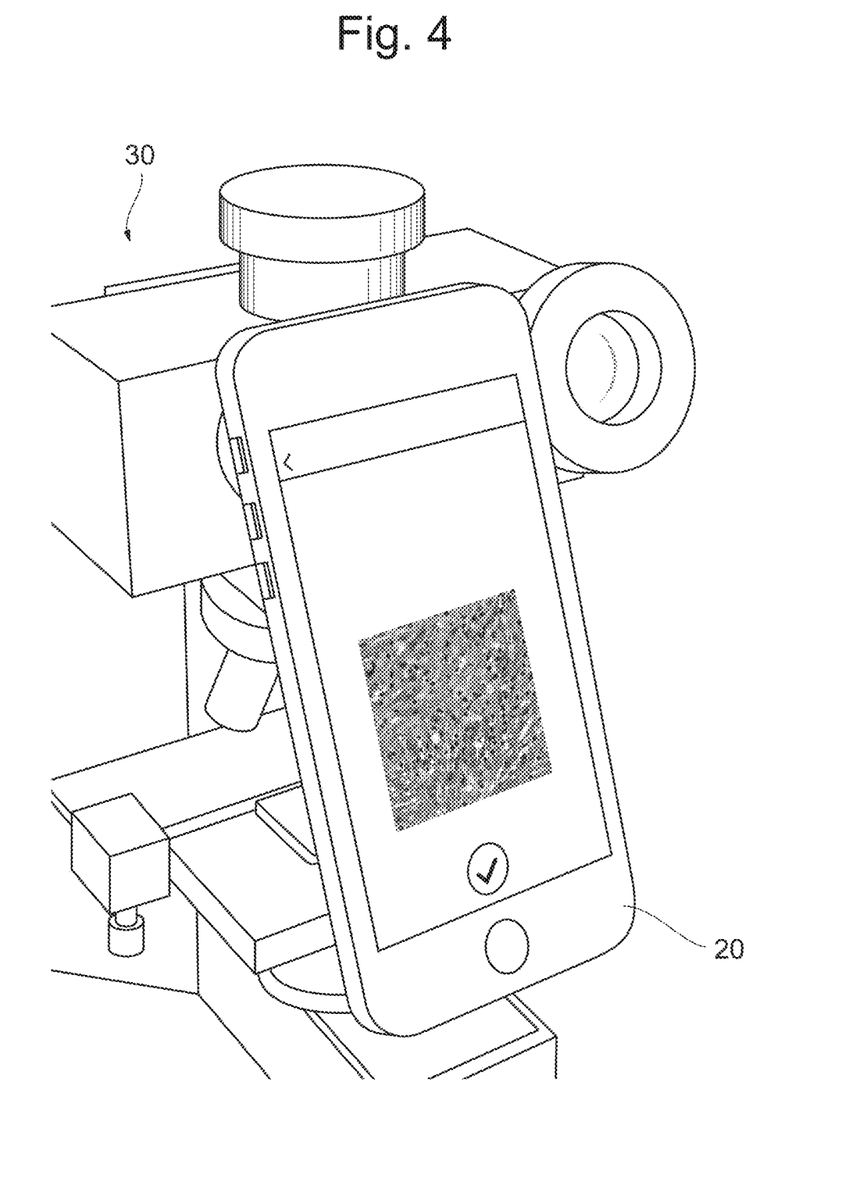
FIG. 4 is a diagram illustrating an example of taking a pathological image by using a user terminal according to the present embodiment.

FIG. 4 is a diagram illustrating an example of taking a pathological image by using the user terminal 20 according to the present embodiment. The user observes pathological tissue with the microscope 30 and takes the pathological image by using the user terminal 20 such as the smartphone. The pathological image may be taken by applying an imaging unit of the user terminal 20 to an eyepiece of the microscope 30, or may be taken by an imaging unit provided in the microscope 30.

The pathological image taken by using the user terminal 20 is transmitted to the image extraction device 10 through the communication network N. The user terminal 20 may also transmit, to the image extraction device 10, one or more pathological images selected by the user from among a plurality of taken pathological images.

Figure 5:
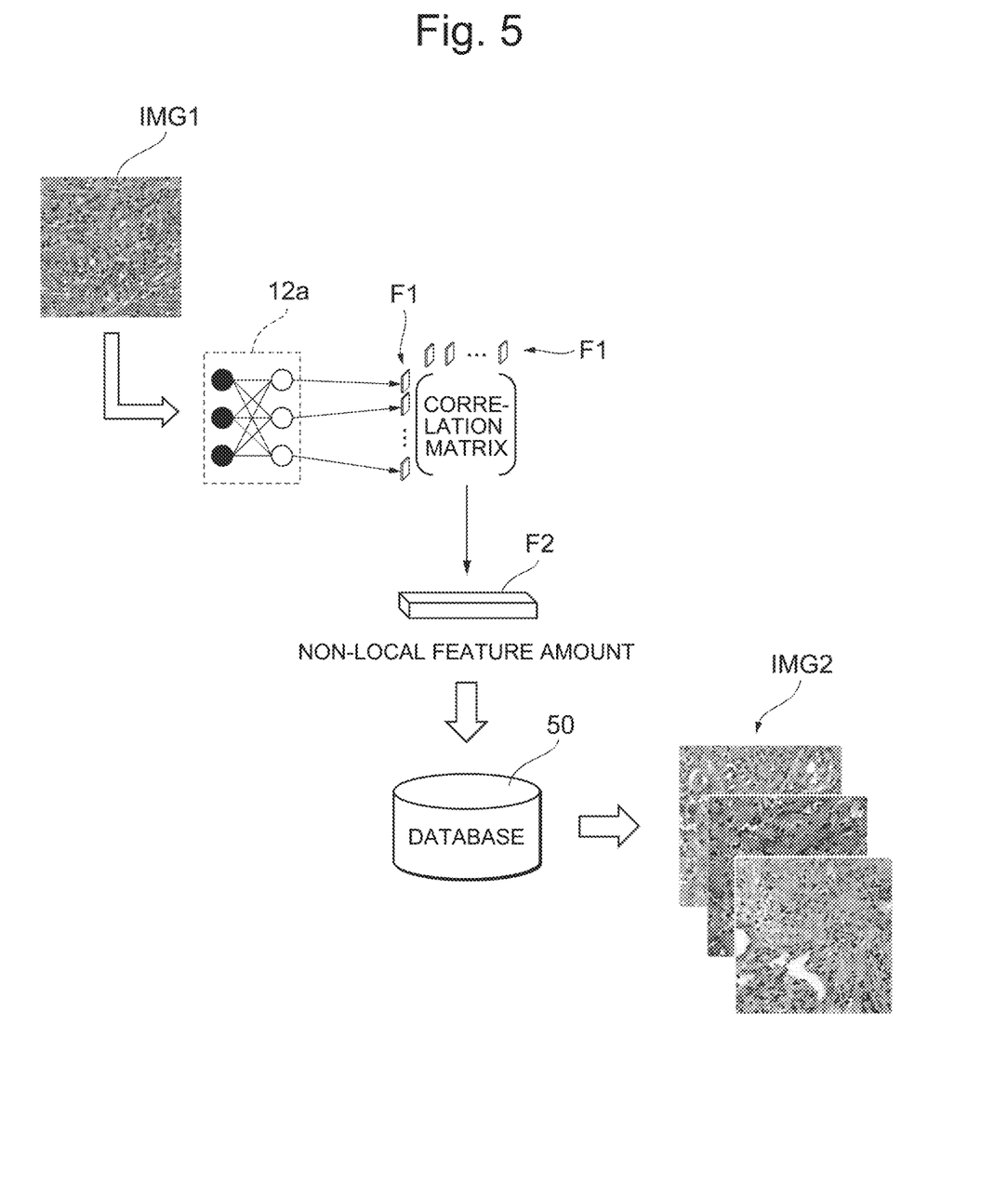
FIG. 5 is a diagram illustrating an outline of processing by the image extraction device according to the present embodiment to extract reference images similar to the pathological image.

FIG. 5 is a diagram illustrating an outline of processing by the image extraction device 10 according to the present embodiment to extract reference images IMG2 similar to a pathological image IMG1. The image extraction device 10 inputs the acquired pathological image IMG1 to the convolutional neural network 12a to calculate feature maps F1.

Then, the image extraction device 10 calculates a correlation matrix of the calculated feature maps F1 to calculate a non-local feature amount F2 by using Compact Bilinear Pooling. But the image extraction device 10 may calculate the non-local feature amount F2 from the correlation matrix of the feature maps F1 by any other method such as principal component analysis. When the non-local feature amount F2 is calculated from the correlation matrix of the feature maps F1, the image extraction device 10 may use any method to reduce the data dimensions.

The image extraction device 10 calculates a degree of similarity between the non-local feature amount F2 of the pathological image IMG1 and each of non-local feature amounts of the reference images IMG2 stored in the database 50 to extract one or more reference images IMG2 higher in degree of similarity. With the one or more reference images IMG2, the identification information of the TCGA and information related to the type of pathology may be associated. The user visually compares the pathological image IMG1 and the extracted reference images IMG2 to diagnose the type of pathology related to tissue captured in the pathological image IMG1.

Figure 6:
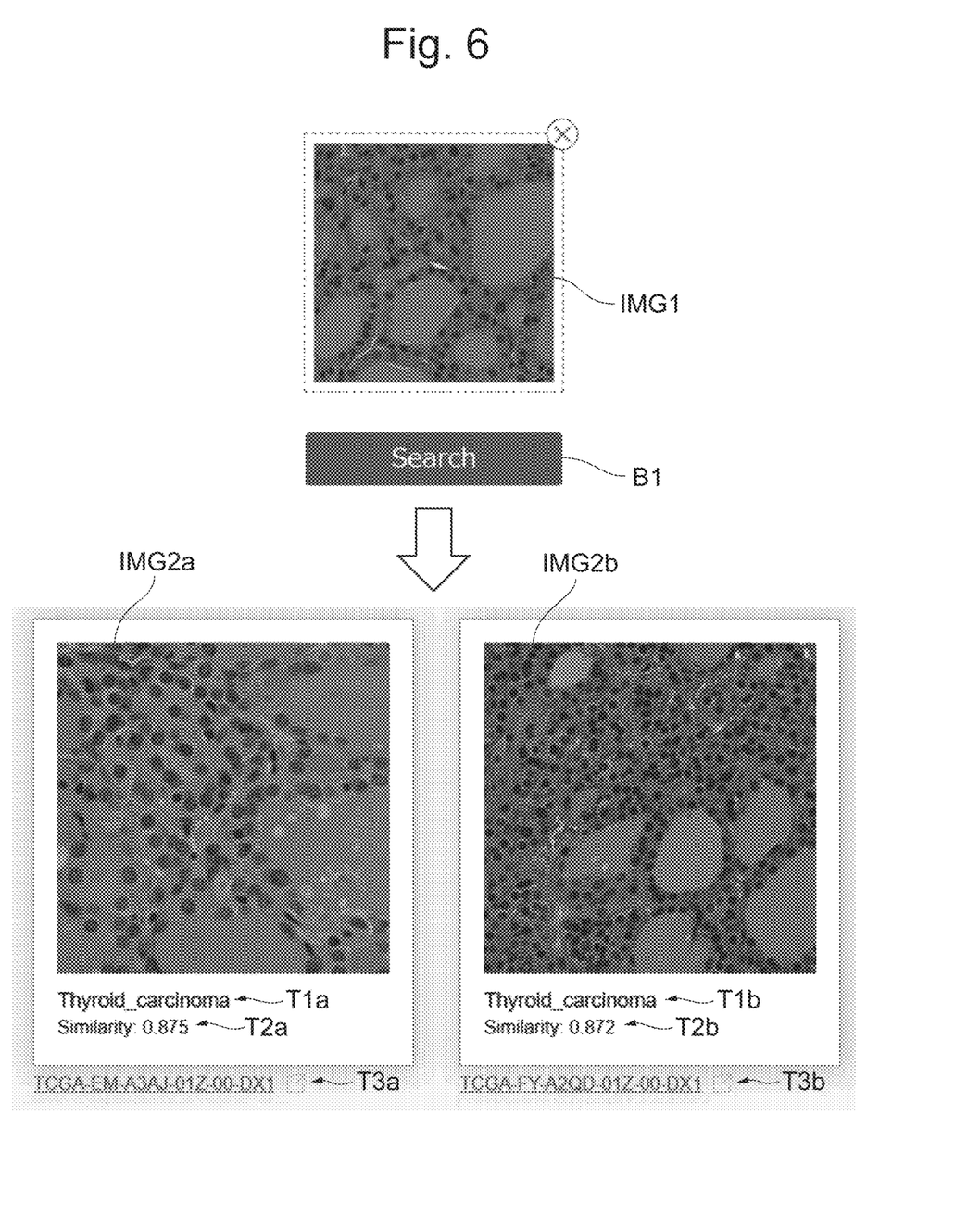
FIG. 6 is a diagram illustrating an example of the reference images extracted by the image extraction device according to the present embodiment.

FIG. 6 is a diagram illustrating an example of reference images IMG2 extracted by the image extraction device 10 according to the present embodiment. In FIG. 6, the pathological image IMG1 as a query and a first reference image IMG2a and a second reference image IMG2b extracted by the image extraction device 10 are illustrated.

The user terminal 20 accepts the selection of the pathological image IMG1 as the query, and displays, on the display unit, the pathological image IMG1 and a search button B1 labeled with "Search." When the search button B1 is tapped by the user, the pathological image IMG1 is transmitted from the user terminal 20 to the image extraction device 10, and the image extraction device 10 extracts similar reference images from the database 50.

The first reference image IMG2a and the second reference image IMG2b are an example of reference images extracted by the image extraction device 10 when the pathological image IMG1 is set as the query. A type of pathology T1a written as "Thyroid_carcinoma" (thyroid carcinoma), a degree of similarity T2a written as "Similarity: 0.875," and a TOGA identification information T3a written as "TOGA-EM-A3AJ-01Z-00-DX1" are displayed at the bottom of the first reference image IMG2a. Further, a type of pathology T1b written as "Thyroid_carcinoma" (thyroid carcinoma), a degree of similarity T2b written as "Similarity: 0.872," and a TOGA identification information T3b written as "TOGA-FY-A2QD-01Z-00-DX1" are displayed at the bottom of the second reference image IMG2b. These pieces of information may be displayed on the display unit 10f of the image extraction device 10, or displayed on the display unit of the user terminal 20.

Thus, the appropriate reference images IMG2 can be extracted from the database 50 by using the pathological image IMG1 as the query. Further, information related to the extracted one or more reference images IMG2 can be checked, and this can make it easier to evaluate a relation with the pathological image IMG1 as the query.

Figure 7:
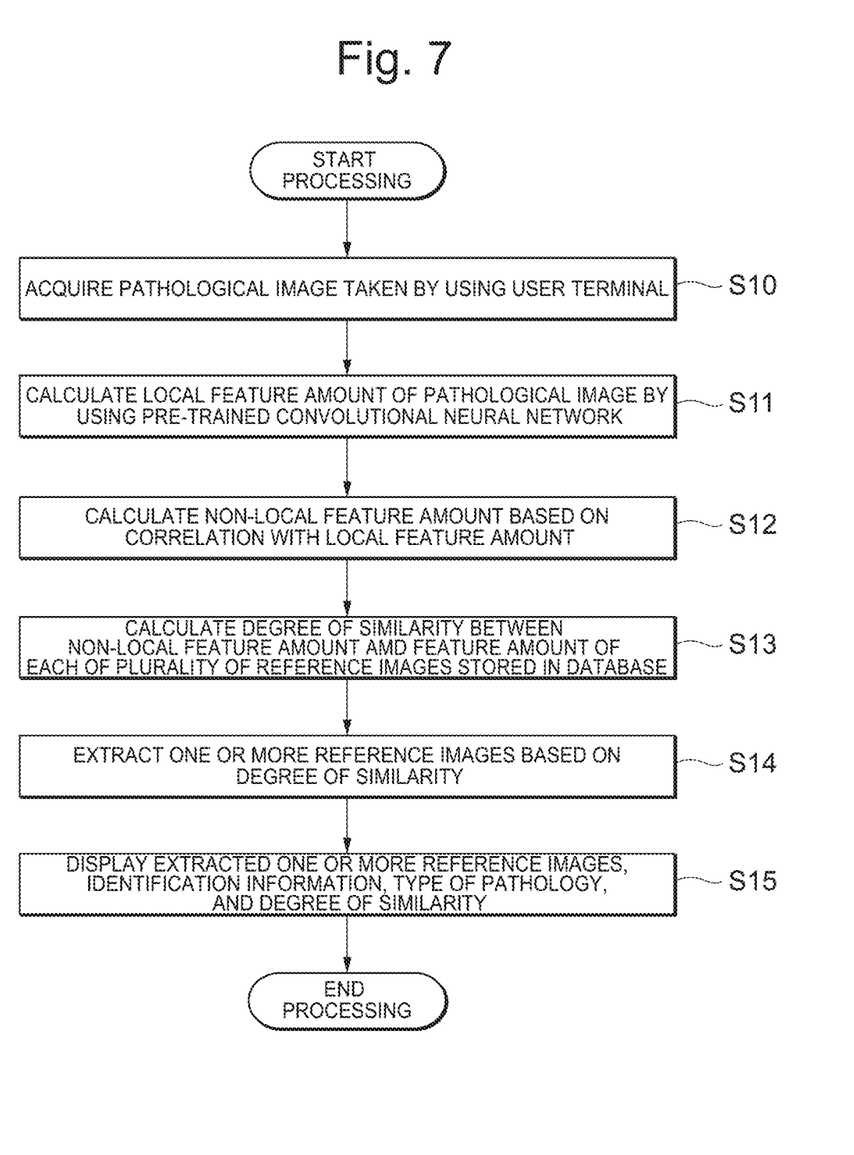
FIG. 7 is a flowchart of extraction processing executed by the image extraction device according to the present embodiment.

FIG. 7 is a flowchart of extraction processing executed by the image extraction device 10 according to the present embodiment. First, the image extraction device 10 acquires a pathological image taken by the user terminal 20 (S10).

Next, the image extraction device 10 calculates a local feature amount of the pathological image by using the pre-trained convolutional neural network 12a (S11), and calculates a non-local feature amount based on a correlation with the local feature amount (S12).

After that, the image extraction device 10 calculates a degree of similarity between the non-local feature amount and a feature amount of each of a plurality of reference images stored in the database 50 (S13) to extract one or more reference images based on the degree of similarity (S14).

Finally, the image extraction device 10 displays, on at least either one of the display unit of the user terminal 20 or the display unit 10f of the image extraction device 10, the extracted one or more reference images, the identification information, the type of pathology, and the degree of similarity (S15).

Figure 8:
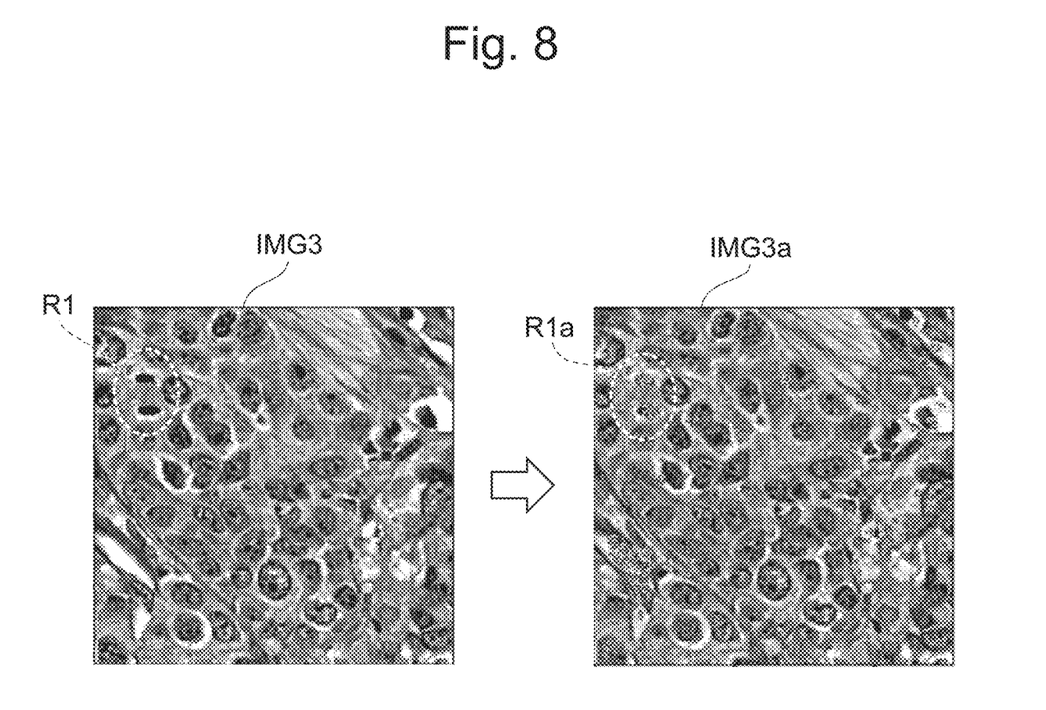
FIG. 8 is a diagram illustrating an example of a region of a pathological image as the basis of determination on a gene mutation by the image extraction device according to the present embodiment.

FIG. 8 is a diagram illustrating an example of a region of a pathological image as the basis of the determination on a gene mutation by the image extraction device 10 according to the present embodiment. In FIG. 8, a pathological image IMG3, in which it is determined by the determination model 12b that a certain gene mutation occurs in a cell, and an image IMG3a, in which a region of the pathological image as the basis of the determination is represented by a heat map, are illustrated. Note that the pathological image IMG3 is a pathological image of breast cancer, and a p53 gene mutation occurs in this example.

For example, divided nuclei are captured in a region R1 of the pathological image IMG3, and it can be read from a region R1a of the image IMG3a that the determination model 12b determines that a certain gene mutation occurs in the cell on the basis of the divided nuclei. However, it is not always easy to interpret all points to which the determination model 12b pays attention, and some of them may be difficult to interpret.

In FIG. 8, although the example in which the certain gene mutation occurs in the cell is illustrated, even in a pathological image with no certain cell gene mutation determined by the determination model 12b, the region in the pathological image as the basis of the determination can also be represented as a heat map.

Figure 9:
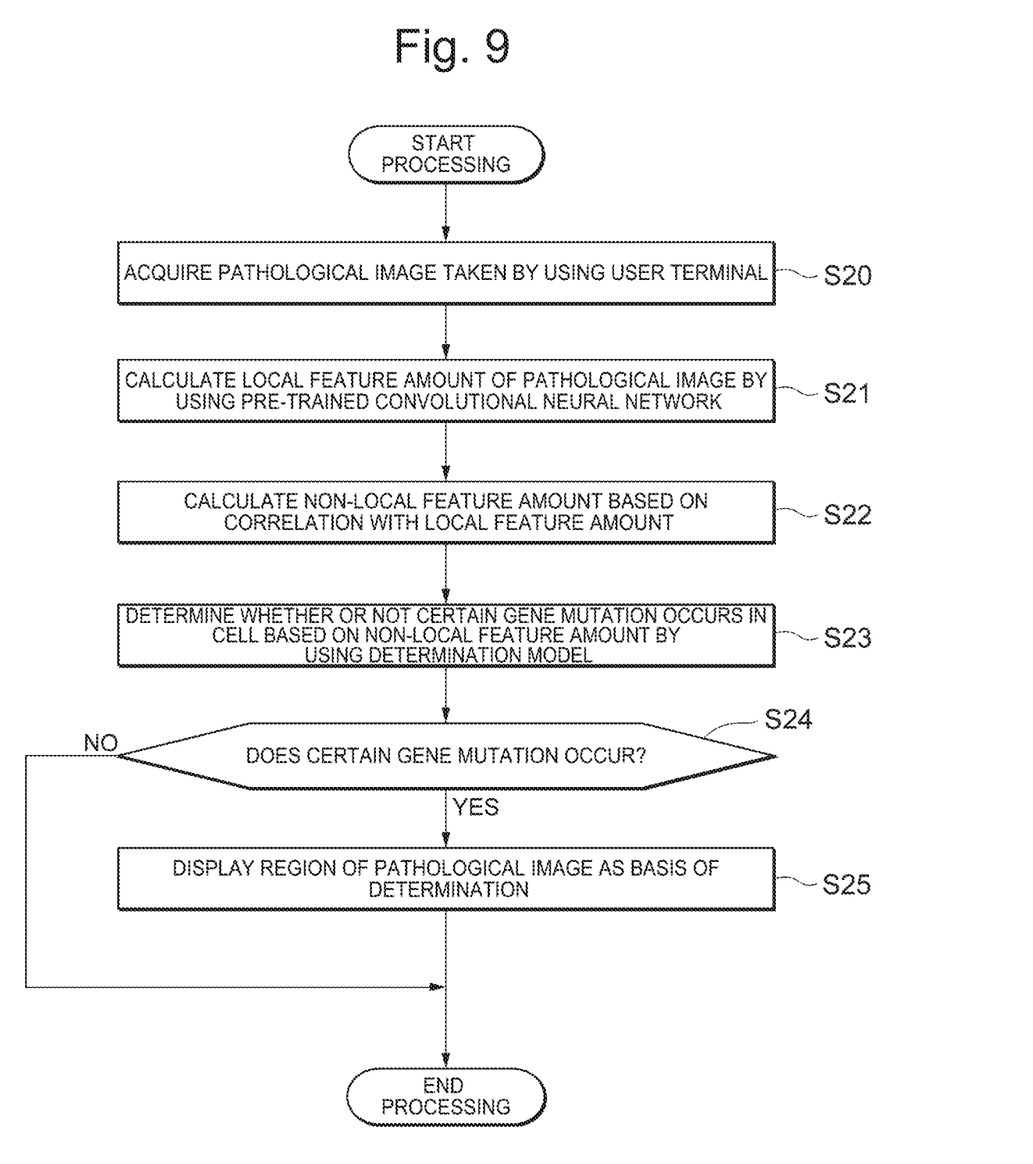
FIG. 9 is a flowchart of processing executed by the image extraction device according to the present embodiment to determine the presence or absence of a gene mutation.

FIG. 9 is a flowchart of processing executed by the image extraction device 10 according to the present embodiment to determine the presence or absence of a gene mutation. First, the image extraction device 10 acquires a pathological image taken by the user terminal 20 (S20).

Next, the image extraction device 10 calculates a local feature amount of the pathological image by the pre-trained convolutional neural network 12a (S21), and calculates a non-local feature amount based on a correlation with the local feature amount (S22).

After that, the image extraction device 10 determines whether or not a certain gene mutation occurs in a cell based on the non-local feature amount by using the determination model 12b (S23).

When it is determined that the certain gene mutation occurs (S24: YES), the image extraction device 10 calculates and displays a region of the pathological image as the basis of the determination (S25).

Figure 10:
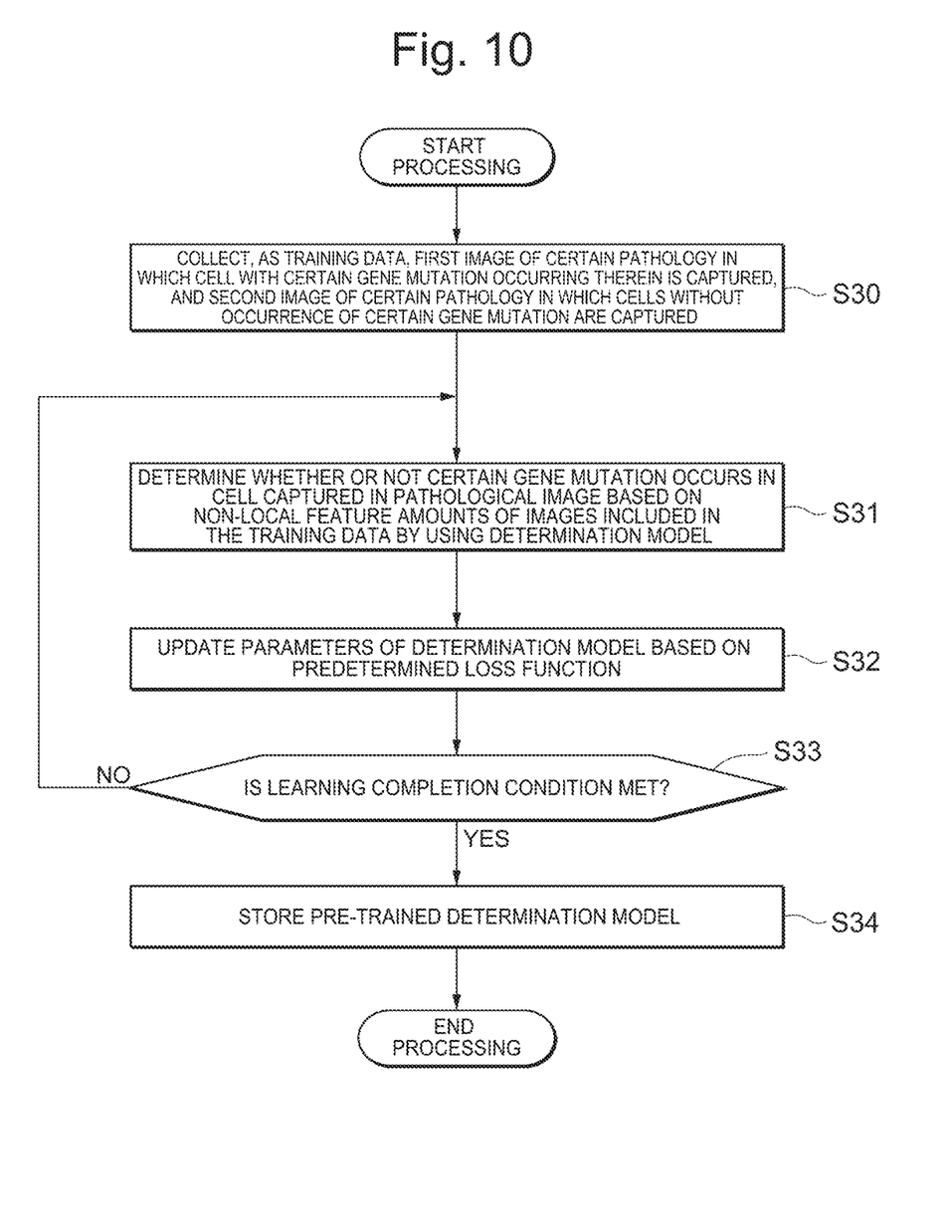
FIG. 10 is a flowchart of determination model generation processing executed by the image extraction device according to the present embodiment.

FIG. 10 is a flowchart of determination model generation processing executed by the image extraction device 10 according to the present embodiment. The image extraction device 10 collects, as training data, a first image of a certain pathology in which a cell with a certain gene mutation occurring therein is captured, and a second image of the certain pathology in which cells without occurrence of the certain gene mutation are captured (S30).

Then, the image extraction device 10 determines whether or not the certain gene mutation occurs in a cell captured in the pathological image based on the non-local feature amounts of images included in the training data by the determination model 12b (S31). The image extraction device 10 updates the parameters of the determination model 12b based on a predetermined loss function. For example, the image extraction device 10 may use cross-entropy as the loss function to update the parameters of the neural network that constitute the determination model 12b by a backpropagation method.

When a learning completion condition is not met (S33: NO), the image extraction device 10 executes the processes S31 and S32 again. Here, the learning completion condition may be that the value of the loss function be a predetermined value or less, or that the number of executions of the processes S31 and S32 be a predetermined number of times or more.

On the other hand, when the learning completion condition is met (S33: YES), the image extraction device 10 stores the pre-trained determination model 12b in the storage unit 12 (S34), and ends the determination model generation processing.

The embodiment described above is to make it easier to understand the present invention, and not to interpret the present invention in a limited way. Each of the elements included in the embodiment, the arrangement, materials, conditions, and sizes of the elements are not limited to those exemplified, and can be changed as appropriate. Further, configurations illustrated in different embodiments can also be partially replaced or combined.

REFERENCE SIGNS LIST

10 . . . image extraction device, 10a . . . CPU, 10b . . . RAM, 10c . . . ROM, 10d . . . communication unit, 10e . . . input unit, 10f . . . display unit, 11 . . . acquisition unit, 12 . . . storage unit, 12a . . . CNN, 12b . . . determination model, 13 . . . first calculation unit, 14 . . . second calculation unit, 15 . . . third calculation unit, 16 . . . extraction unit, 17 . . . determination unit, 18 . . . generation unit, 20 . . . user terminal, 30 . . . microscope, 50 . . . database, 100 . . . image extraction system.

What is claimed is:

1. An image extraction device comprising:
an acquisition unit which acquires a pathological image;
a first calculation unit which calculates a local feature amount of the pathological image;
a second calculation unit which calculates a non-local feature amount by performing calculation processing to reduce a dimension of a correlation matrix of the local feature amount;
a third calculation unit which calculates a degree of similarity between the non-local feature amount and a feature amount of each of a plurality of reference images stored in a database; and
an extraction unit which extracts one or more reference images based on the degree of similarity.

2. The image extraction device according to claim 1, further comprising a display unit which displays at least either one of the extracted one or more reference images, identification information of the one or more reference images, a type of pathology related to the one or more reference images, and the degree of similarity between the one or more reference images and the pathological image.

3. The image extraction device according to claim 1, wherein the first calculation unit calculates the local feature amount using a feature map calculated by a hidden layer included in a pre-trained convolutional neural network.

4. The image extraction device according to claim 1, wherein the second calculation unit calculates the non-local feature amount based on a correlation with a feature map calculated by a hidden layer included in a pre-trained convolutional neural network.

5. The image extraction device according to claim 1, wherein the second calculation unit calculates the non-local feature amount based on a correlation between two kinds of feature maps calculated by different hidden layers included in a pre-trained convolutional neural network.

6. The image extraction device according to claim 1, wherein the second calculation unit calculates the non-local feature amount based on a correlation between two kinds of feature maps calculated by hidden layers included in two kinds of pre-trained convolutional neural networks.

7. The image extraction device according to claim 1, wherein the plurality of reference images includes images cut out at random from regions selected in a whole slide image of pathological tissue.

8. The image extraction device according to claim 1, further comprising a determination unit which determines whether or not a certain gene mutation occurs in a cell captured in the pathological image based on the non-local feature amount.

9. The image extraction device according to claim 8, further comprising a generation unit which uses, as training data, a first image of a certain pathology, in which a cell with a certain gene mutation occurring therein is captured, and a second image of the certain pathology, in which cells without occurrence of the certain gene mutation are captured, to generate a determination model used to determine whether or not the certain gene mutation occurs in a cell captured in the pathological image based on the non-local feature amount.

10. The image extraction device according to claim 9, further comprising a display unit which, when it is determined by the determination model that the certain gene mutation occurs, displays a region of the pathological image as the basis of the determination.

11. An image extraction system including an image extraction device and a user terminal, wherein
the user terminal has an imaging unit for taking a pathological image, and
the image extraction device has:
an acquisition unit which acquires the pathological image;
a first calculation unit which calculates a local feature amount of the pathological image;
a second calculation unit which calculates a non-local feature amount by performing calculation processing to reduce a dimension of a correlation matrix of the local feature amount;
a third calculation unit which calculates a degree of similarity between the non-local feature amount and a feature amount of each of a plurality of reference images stored in a database; and
an extraction unit which extracts one or more reference images based on the degree of similarity.

12. The image extraction system according to claim 11, wherein the user terminal further has a display unit which displays at least either one of the extracted one or more reference images, identification information of the one or more reference images, a type of pathology related to the one or more reference images, and the degree of similarity between the one or more reference images and the pathological image.

13. An image extraction method comprising:
acquiring a pathological image;
calculating a local feature amount of the pathological image;
calculating a non-local feature amount by performing calculation processing to reduce a dimension of a correlation matrix of the local feature amount;
calculating a degree of similarity between the non-local feature amount and a feature amount of each of a plurality of reference images stored in a database; and
extracting one or more reference images based on the degree of similarity.

14. A non-transitory computer readable medium storing an image extraction program causing an arithmetic unit included in an image extraction device to function as:
an acquisition unit which acquires a pathological image;
a first calculation unit which calculates a local feature amount of the pathological image;
a second calculation unit which calculates a non-local feature amount by performing calculation processing to reduce a dimension of a correlation matrix of the local feature amount;
a third calculation unit which calculates a degree of similarity between the non-local feature amount and a feature amount of each of a plurality of reference images stored in a database; and
an extraction unit which extracts one or more reference images based on the degree of similarity.

* * * * *